(12) United States Patent
Kaminuma et al.

(10) Patent No.: US 8,138,374 B2
(45) Date of Patent: Mar. 20, 2012

(54) COMPOSITION FOR EXTERNAL APPLICATION TO SKIN

(75) Inventors: Mikiko Kaminuma, Kanagawa (JP); Masaru Suetsugu, Kanagawa (JP); Nobuhiko Ochiai, Kanagawa (JP); Makoto Tsunenaga, Kanagawa (JP)

(73) Assignee: Shiseido Company, Ltd., Tokyo (JP)

( * ) Notice: Subject to any disclaimer, the term of this patent is extended or adjusted under 35 U.S.C. 154(b) by 412 days.

(21) Appl. No.: 12/449,143

(22) PCT Filed: Jan. 24, 2008

(86) PCT No.: PCT/JP2008/051000
§ 371 (c)(1), (2), (4) Date: Jul. 24, 2009

(87) PCT Pub. No.: WO2008/090962
PCT Pub. Date: Jul. 31, 2008

(65) Prior Publication Data
US 2010/0094054 A1    Apr. 15, 2010

(30) Foreign Application Priority Data
Jan. 25, 2007    (JP) .................................. 2007-015083

(51) Int. Cl.
*C07C 233/05* (2006.01)
*A61K 31/16* (2006.01)

(52) U.S. Cl. .......... 564/197; 514/626; 424/401
(58) Field of Classification Search .......... 564/197; 514/626; 424/401
See application file for complete search history.

(56) References Cited

U.S. PATENT DOCUMENTS
4,623,486 A    11/1986    Lombardino
7,078,047 B2    7/2006    Philippe et al.

FOREIGN PATENT DOCUMENTS
JP    61-277683 A    12/1986
JP    2000-178118 A    6/2000
JP    2002-308756 A    10/2002

OTHER PUBLICATIONS

International Search Report mailed Mar. 11, 2008, in prior PCT/JP2008/051000, 2 pages.

*Primary Examiner* — Shailendra Kumar
(74) *Attorney, Agent, or Firm* — Foley & Lardner LLP

(57) ABSTRACT

The present invention provides a composition for external application to skin containing one type or two or more types of compounds selected from the group consisting of aminoacetoamide compounds represented by the following general formula (1) and salts thereof.

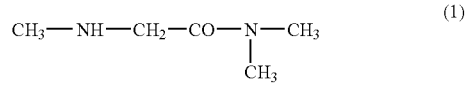

(1)

3 Claims, 2 Drawing Sheets

※NUMBERS INDICATE WRINKLE SURFACE AREA RATIO

《0M》 (COMPARATIVE EXAMPLE 3) 19.32%   《1M》 (COMPARATIVE EXAMPLE 3) 20.38%

《0M》 (EXAMPLE 2) 12.36%   《1M》 (EXAMPLE 2) 10.15%

COMPOSITION FOR EXTERNAL APPLICATION TO SKIN

CROSS-REFERENCE TO RELATED APPLICATIONS

This application is a National Stage application of PCT/JP2008/051000, filed Jan. 24, 2008, which claims priority from Japanese application JP 2007-015083, filed Jan. 25, 2007.

TECHNICAL FIELD

The present invention relates to a composition for external application to skin.

More particularly, the present invention relates to a moisturizer having superior feel during use, superior penetrability and superior sustained moisturizing effects by acting directly on the corneal layer and increasing moisture content therein, a wrinkle preventive/improver having superior effects, and a composition for external application to skin having wrinkle preventive/improving effects that increases moisture in the corneal layer by acting directly on the corneal layer, has superior stability and has superior usability.

BACKGROUND ART

Although aging progresses in organs throughout the body, its effects can be observed particularly in the skin, and with respect to the face in particular where attention tends to be easily focused, wrinkles and crow's feet that occur with aging cause concern for many middle-aged and elderly persons, and especially women. There has conventionally been a strong demand for cosmetics for improving such wrinkles, and although various efforts have been made thus far in response thereto, since there are many aspects of the mechanism relating to aging and wrinkles that remain unclear, an invention yielding satisfactory effects has yet to be realized. On the other hand, since retention of moisture by the outermost layer of the epidermis known as the corneal layer keeps the skin flexible, gives it elasticity and protects the dermis, certain objectives were expected to be achieved.

Amidst these circumstances, compositions for external application to skin have conventionally incorporated moisturizers for the purpose of improving usability and safety and preventing putrefaction and the like in addition to demonstrating moisturizing effects, examples of which include polyols and polyethers of glycerin, 1,3-butylene glycol, xylitol, sorbitol, erythritol, maltitol, polyethylene glycol, propylene glycol or diglycerin-(EO)/(PO) addition products and the like. Although these substances have moisturizing effects, their effects for preventing and/or improving wrinkles are inadequate, while further having problems with usability such as stickiness as well as problems such as the generation of odors as a result of oxidation.

In addition, polymer compounds of hyaluronic acid, mucoitin sulfate, trichosanic acid, chondroitin sulfate, soluble collagen or atherocollagen and the like are also used as moisturizers. Although these have higher moisturizing effects than polyols and the like, their moisturizing effects are still inadequate for preventing and/or improving wrinkles. In addition, since their effects are based on moisture retention by the skin's surrounding environment, polymer compounds have inferior penetrability into the skin and do not act directly within skin. In addition, these polymer compounds also have problems of requiring excessive time for neutralization and dissolution during their incorporation, as well as problems with usability in terms of causing tightness by creating the sensation of a coating on the skin and being even stickier than polyols.

Examples of low molecular weight compounds other than polyols widely used as moisturizers include sodium lactate, bile acid salts, pyrrolidone carboxylates and amino acids. Since these are low molecular weight compounds, although they have the potential to demonstrate their own functions by penetrating into the corneal layer, their own moisturizing effects are not that high and are inadequate for preventing and/or improving wrinkles. Sarcosine is an example of a moisturizer that that improves the moisture retention and moisture absorption properties of the compound itself (Patent Document 1). Although this compound itself has moisture absorbing properties, since it does not act directly on moisture retention in the skin (moisture in the corneal layer), moisturizing effects are inadequate for preventing and/or improving wrinkles. Moreover, since these compounds, including sarcosine, have high crystallinity and low solubility in substances other than water, when incorporated in compositions for external application to skin having a low moisture content, they end up precipitating with the evaporation of moisture following their application, thereby resulting in the problems of having inferior sustained moisturizing effects as well as inhibiting penetration into the corneal layer. Moreover, not only is it difficult to incorporate large amounts of these compounds in preparations such as milky lotions and creams containing low amounts of water, since the solubility of these compounds is inferior even in ethanol, they also have the problem of inferior low-temperature stability in cosmetic lotions having a high ethanol content.

As a result of conducting extensive research in consideration of the aforementioned circumstances on substances that have moisturizing effects to a degree to which wrinkle preventing and/or improving effects are expected, do not precipitate following application of a composition for application to skin, have superior penetrability, increase the moisture content in the corneal layer by acting directly on the corneal layer, and result in superior stability for the composition for application to skin in which they are incorporated, the inventors of the present invention found that aminoacetoamide compounds of the present invention and salts thereof demonstrate superior moisturizing effects, have high penetrability, increase moisture content in the corneal layer by acting directly on the corneal layer, have superior anti-wrinkle effects, have superior water solubility, and also have superior solubility in substances other than water, while also facilitating preparation of compositions for external application to skin and resulting in superior stability of the prepared compositions for external application to skin, thereby leading to completion of the present invention.

Patent Document 1: Japanese Patent Publication No. 3441387

DISCLOSURE OF THE INVENTION

Problems to be Solved by the Invention

The present invention provides a moisturizer having superior feel during use, superior penetrability and superior sustained moisturizing effects by acting directly on the corneal layer and increasing moisture content therein, a wrinkle preventive/improver having superior effects, and a composition for external application to skin having wrinkle preventive/ improving effects that increases moisture in the corneal layer by acting directly on the corneal layer, has superior stability and has superior usability.

Means for Solving the Problems

Namely, the present invention provides a moisturizer containing one type or two or more types of compounds selected from the group consisting of aminoacetoamide compounds represented by the following general formula (1) and salts thereof.

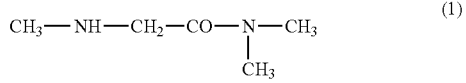

$$CH_3—NH—CH_2—CO—N—CH_3 \atop | \atop CH_3 \qquad (1)$$

In addition, the present invention provides a composition for external application to skin having moisturizing effects and wrinkle preventive/improving effects that has superior skin penetrability, increases moisture content in the corneal layer by acting directly thereon, has superior stability and has superior usability, comprising a compound selected from the group consisting of aminoacetoamide compounds represented by general formula (1) and salts thereof.

Effects of the Invention

According to the present invention, a moisturizer having superior moisture retention effects, superior feel during use, superior penetrability and sustained moisturizing effects by acting directly on the corneal layer and increasing moisture content therein, a wrinkle preventive/improver having superior effects, and a composition for external application to skin having moisturizing effects and wrinkle preventive/improving effects that increases moisture in the corneal layer by acting directly on the corneal layer, has superior stability and has superior usability, can be provided.

BEST MODE FOR CARRYING OUT THE INVENTION

Figure 1:
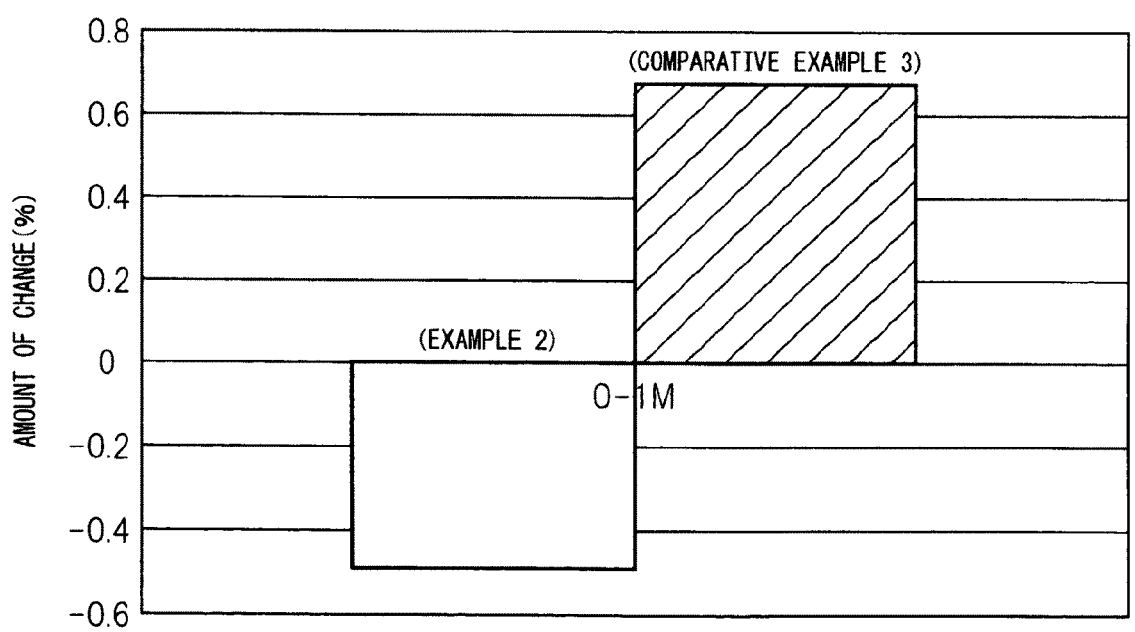
FIG. 1 shows the results of analyzing wrinkle morphology from images as measured with a Primos followed by calculation of wrinkle surface area ratio. The results are shown as the difference between wrinkle surface area ratio before continuous application and wrinkle surface area ratio after continuous application.

The moisturizer of the present invention comprises one or more types of an aminoacetoamide compound represented by the aforementioned general formula (1) or a salt thereof. The wrinkle preventive/improver of the present invention comprises one or more types of an aminoacetoamide compound represented by the general formula (1) or a salt thereof as an active ingredient having wrinkles preventive and/or improving effects. In addition, the composition for external application to skin of the present invention comprises one or more types of an aminoacetoamide compound represented by the general formula (1) or a salt thereof.

The aminoacetoamide compound represented by the general formula (1) used in the present invention is a known compound used under a chemical name such as N,N-dimethyl-2-(methylamino) acetoamide or N',N'-dimethyl sarcosine amide. Although its hydrochlorides are known to be used as intermediates of benzothiazine dioxide derivatives (Japanese Unexamined Patent Publication No. S61-277683), its possession of moisturizing effects of the present invention is a novel finding, its possession of wrinkle preventive/improving effects is also a novel finding, and its use in a composition for external application to skin is a novel usage.

The N,N-dimethyl-2-(methylamino) acetoamide used in the present invention can be easily synthesized, and is commercially available from manufacturers such as Bachem AG.

There are no particular limitations on the salts of the aminoacetoamide compound represented by the general formula (1), and examples include, but are not limited to, salts of acids such as hydrochloric acid, sulfuric acid, phosphoric acid, hydrobromic acid, alkyl sulfates such as methyl sulfate or p-toluenesulfonic acid, acetic acid, lactic acid, maleic acid, fumaric acid, oxalic acid, succinic acid, tartaric acid or citric acid, and amino acids such as betaine, glycine, alanine, serine, taurine, glutamic acid or aspartic acid.

In the present invention, the incorporated amount of the aminoacetoamide compound represented by the general formula (1) or salt thereof is 0.001 to 20.0% by weight and preferably 0.1 to 10.0% by weight based on the total weight of the moisturizer or composition for external application to skin. If the incorporated amount thereof is less than 0.001% by weight, the resulting effects are lacking, while additional effects cannot be expected even if incorporated in amount exceeding 20.0% by weight.

The composition as claimed in the present invention can be produced in accordance with conventional methods, and although the composition can be prepared with the only component comprising the composition consisting of one type or two or more types of the aminoacetoamide compound represented by the general formula (1) or salt thereof, components conventionally used in skin preparations for external use such as cosmetics or pharmaceuticals containing over-the-counter drugs are suitably incorporated as necessary, examples of which include oils, surfactants, powders, colorants, water, alcohols, thickeners, chelating agents, silicones, antioxidants, ultraviolet absorbers, moisturizers, fragrances, various pharmaceutically effective components, preservatives, pH adjusters and neutralizers.

Among the examples of arbitrarily incorporated components suitably incorporated in the aforementioned composition, examples of oils include higher alcohols such as lauryl alcohol, cetyl alcohol, stearyl alcohol, myristyl alcohol, oleyl alcohol and other linear alcohols or monostearyl glycerin ether, lanolin alcohol, cholesterol, phytosterol, isostearyl alcohol and other branched alcohols, higher fatty acids such as lauric acid, myristic acid, palmitic acid or stearic acid, waxes such as solid paraffin, beeswax, hydrogenated castor oil, carnauba wax or barico wax, animal and vegetable oils and fats such as beef tallow, pork tallow, goat tallow, squalane, coconut oil, palm oil, palm kernel oil, soybean oil, olive oil, cottonseed oil, jojoba oil, castor oil or lanolin, mineral oils such as liquid paraffin or vaseline, and synthetic oils such as trimethylpropane triisostearate, isopropyl myristate, glycerol tri-2-ethylhexanate, pentaerythritol tetra-2-ethylhexanate, silicone oil, or polyoxyethylene (abbreviated as POE) polyoxypropylene (abbreviated as POP) pentaerythritol ether.

Examples of surfactants include anionic surfactants, including fatty acid soaps such as soap base, sodium laurate or sodium palmitate, higher alkyl sulfate ester salts such as sodium lauryl sulfate or potassium lauryl sulfate, alkyl ether sulfate ester salts such as POE lauryl sulfate triethanolamine or POE sodium lauryl sulfate, N-acylsarcosinic acids such as sodium lauryl sarcosine, higher fatty acid amide sulfonates such as sodium N-myristyl-N-methyl taurine or sodium coconut oil fatty acid methyl tauride, phosphate ester salts such as POE stearyl ether phosphate, sulfosuccinates such as sodium monolauroyl monoethanol amide POE sulfosuccinate or sodium lauryl polypropylene glycol sulfosuccinate, alkyl benzene sulfonates such as sodium linear dodecyl benzene sulfonate or linear dodecyl benzene sulfonate triethanolamine, N-acylglutamates such as disodium N-stearoyl glutamate or monosodium N-stearoyl glutamate, higher fatty acid ester sulfate ester salts such as sodium hydrogenated coconut oil fatty acid glycerin sulfate, sulfated oils such as turkey red oil, POE alkyl ether carboxylic acids, POE alkyl allyl ether carboxylates, higher fatty acid ester sulfonates, secondary alcohol sulfate ester salts, higher fatty acid alkylol amide sulfate ester salts, sodium lauroyl monoethanolamide succinate, and sodium casein.

Other examples of surfactants include cationic surfactants including alkyl trimethyl ammonium salts such as stearyl trimethyl ammonium chloride or lauryl trimethyl ammonium chloride, dialkyl dimethyl ammonium salts such as distearyl dimethyl ammonium chloride, alkyl pyridinium salts such as cetylpyridinium chloride, alkyl quaternary ammonium salts, alkyl dimethyl benzyl ammonium salts, alkyl isoquinolinium salts, dialkyl morphonium salts, POE alkyl amines, alkyl amine salts, polyamine fatty acid derivatives, amyl alcohol fatty acid derivatives and benzalkonium chloride; amphoteric surfactants including imidazoline-based amphoteric surfactants such as 2-cocoyl-2-imidazolinium hydroxide-1-carboxyethyloxy 2 sodium salt and betaine-based surfactants such as amidobetaine or sulfobetaine; lipophilic nonionic surfactants including sorbitan fatty acid esters such as sorbitan monooleate, sorbitan monoisostearate, sorbitan monolaurate, sorbitan monopalmitate or sorbitan trioleate, glycerin polyglycerin fatty acids such as glycerin monocottonseed oil fatty acid, glycerin monostearic acid, glycerin sesquioleate or glycerin monostearate malate, propylene glycol fatty acid ester such as propylene glycol monostearate, hydrogenated castor oil derivatives, glycerin alkyl ethers and POE-methylpolysiloxane copolymers; and, hydrophilic nonionic surfactants including POE sorbitan fatty acid esters such as POE sorbitan monooleate or POE sorbitan monostearate, POE sorbitol fatty acid esters such as POE sorbitol monolaurate, POE sorbitol monooleate or POE sorbitol monostearate, POE glycerin fatty acid esters such as POE glycerin monooleate or POE glycerin distearate, POE fatty acid esters such as POE monooleate, POE distearate or POE monodioleate, POE alkyl ethers such as POE lauryl ether, POE oleyl ether or POE cholestanol ether, POE alkyl phenyl ethers such as POE octyl phenyl ether or POE nonyl phenyl ether, pluaronic types such as pluaronic, POE-POP alkyl ethers such as POE-POP monobutyl ether, POE-POP cetyl ether or POE-POP glycerin ether, POE-castor oil hydrogenated castor oil derivatives such as POE castor oil, POE hydrogenated castor oil, POE hydrogenated castor oil monoisostearate or POE hydrogenated castor oil maleic acid, POE beeswax/lanolin derivatives such as POE sorbitol beeswax, alkanol amides such as coconut oil fatty acid diethanol amide or fatty acid isopropanol amide, POE propylene glycol fatty acid esters, POE fatty acid amides, POE alkyl amines, sucrose fatty acid esters and alkyl ethoxy dimethylamine oxides.

Examples of alcohols include lower alcohols such as ethanol, propanol or isopropanol.

Examples of thickeners include water-soluble polymers including vegetable-based polymers such as gum arabic, tragacanth gum, galactan, carob gum, guar gum, carrageenan, pectin, agar or starch (corn, wheat, potato or rice starch), microorganism-based polymers such as dextran or pullulan, starch-based polymers such as carboxymethyl starch or methylhydroxypropyl starch, animal-based polymers such as collagen, casein or gelatin, cellulose-based polymers such as methyl cellulose, nitrocellulose, ethyl cellulose, hydroxyethyl cellulose, sodium cellulose sulfate, hydroxypropyl cellulose, carboxymethyl cellulose or crystalline cellulose, alginic acid-based polymers such as sodium alginate or alginic acid propylene glycol ester, vinyl-based polymers such as polyvinyl methyl ether or carboxyvinyl polymer, POE-based polymers, POE-POP copolymer-based polymers, acrylic-based polymers such as sodium polyacrylate or polyacrylic acid amide, and inorganic water-soluble polymers such as polyethylene imine, cationic polymers, bentonite, magnesium aluminum silicate, laponite, hectolite or silicic anhydride.

Examples of chelating agents include citramalic acid, agalic acid, glyceric acid, shikimic acid, hinokitol, gallic acid, tannic acid, caffeic acid, ethylene diamine tetraacetate, diethylene triamine pentaacetate, phytic acid, polyphosphoric acid, metaphosphoric acid, analogs thereof and alkaline metal salts and carboxylic acid esters thereof.

Examples of ultraviolet absorbers include benzoic acid-based ultraviolet absorbers such as para-aminobenzoic acid, anthranil-based ultraviolet absorbers such as methyl anthranilate, salicylic acid-based ultraviolet absorbers such as octyl salicylate, and cinnamic acid-based ultraviolet absorbers such as isopropyl para-methoxycinnamate or octyl para-methoxycinnamate.

Examples of moisturizers include polyethylene glycol, propylene glycol, dipropylene glycol, 1,3-butylene glycol, glycerin, diglycerin, xylitol, maltitol, maltose, D-mannitol, glucose, fructose, sodium chondroitin sulfate, sodium hyaluronate, sodium lactate, glucosamine and cyclodextrin.

Examples of pharmaceutically effective components able to be incorporated include vitamins such as vitamin A oil, retinol, retinol palmitate, pyridoxine chloride, benzyl nicotinate, nicotinic acid amide, dl-α-tocopherol nicotinate, magnesium ascorbyl phosphate, vitamin D2, dl-α-tocopherol, pantenic acid or biotin, antiinflammatory agents such as azulene or glycyrrhizin, whiteners such as albutin, potassium 4-methoxysalicylate, 2-O-ethylascorbic acid or ascorbic acid glucoside, hormones such as estradiol, astringents such as zinc oxide or tannic acid, refrigerants such as L-methanol or camphor, and other substances such as lysozyme chloride, pyridoxine hydrochloride or sulfur. Moreover, various types of extracts demonstrating various pharmaceutical effects can also be incorporated, examples of which include *Houttunia Cordata* extract, cork tree bark extract, licorice extract, peony root extract, Moutan Cortex extract, Luffa Cylindrica extract, *Saxifraga Sarmentosa* extract, eucalyptus extract, clove extract, horse chestnut extract, *Centaurea Cyanus* Flower extract, algae extract and thyme extract.

Examples of preservatives include para-hydroxybenzoic acid esters such as methyl para-hydroxybenzoate, ethyl para-hydroxybenzoate or butyl para-hydroxybenzoate, benzoic acid, salicylic acid, sorbic acid, parachlorometacresol, hexachlorophene, benzalkonium chloride, chlorohexidine chloride, trichlorocarbanilide, photosensitizers, phenoxyethanol and methylisothiazolinone.

Examples of neutralizers include 2-amino-2-methyl-1-propanol, 2-amino-2-methyl-1,3-propanediol, potassium hydroxide, sodium hydroxide, triethanolamine and sodium carbonate.

Examples of pH adjusters include acetic acid, citric acid, glycolic acid, succinic acid, tartaric acid, malic acid, sodium bicarbonate and ammonium bicarbonate.

Examples of antioxidants include ascorbic acid, α-tocopherol and carotenoids.

The aforementioned components are intended to be exemplary and the present invention is not limited thereto. In addition, these components can be suitably incorporated in combination in accordance with the formula corresponding to the desired form thereof.

There are no particular limitations on the drug form of the moisturizer and composition for external application to skin of the present invention, and any arbitrary drug form can be used, such as a solution system, solubilized system, emulsified system, powder-dispersed system, water-oil bilayer system, water-oil-powder trilayer system, ointment, gel or aerosol. In addition, there are also no particular limitations on the usage form, and any arbitrary usage form can be used, such as a beauty wash, milky lotion, cream, essence, jelly, gel, ointment, pack, mask or foundation.

The moisturizer and composition for external application to skin of the present invention can be used as an aesthetic method for moisturizing skin and preventing the formation or wrinkles and/or reducing or eliminating wrinkles that have formed by applying to the skin. There are no particular limitations on the administration method or dosage of the moisturizer and composition for external application to skin of the present invention in this aesthetic method, and typically a suitable amount, such as 0.1 ml to 1 ml per square centimeter of skin can either be rubbed directly into the skin or that suitable amount can be soaked into a piece of gauze and the like and then affixed to the skin several times per day, and for example, 1 to 5 times per day.

EXAMPLES

The following provides a more detailed explanation of the present invention by listing examples thereof. The present invention is not limited to these examples.

[Skin Corneal Layer Moisturizing Effect Test]

Changes were observed in corneal layer moisture content on the backs of hairless mouse (HR-1, Hoshino Laboratory Animals, Inc.) attributable to application of a drug. The number of test animals was n=5, and corneal layer moisture content was measured using a skin conductor (ASA-MX). After measuring corneal layer moisture content, Example 1, Comparative Example 1 and Comparative Example 2 having the compositions shown below were applied once a day in aliquots of 100 μl each to measurement sites on the backs of the mice. After applying for two consecutive days, corneal layer moisture content was measured on day 3 from the start of testing, after which application was continued for two more consecutive days followed by again measuring corneal layer moisture content on the fifth day from the start of testing.

Example 1

| | |
|---|---|
| N,N-dimethyl-2-(methylamino)acetoamide | 5.0 wt % |
| 1 N hydrochloric acid | For adjusting to pH 7.5 |
| Cosmetic alcohol | 50.0 |
| Purified water | Remainder |

Comparative Example 1

| | |
|---|---|
| Cosmetic alcohol | 50.0 wt % |
| Purified water | Remainder |

Comparative Example 2

| | |
|---|---|
| Glycerin | 5.0 wt % |
| Cosmetic alcohol | 50.0 |
| Purified water | Remainder |

The results for the rate of change (%) in moisture content after application based on a value of 100% for the moisture content before application are shown in the following Table 1.

The moisturizer and composition for external application to skin of the present invention were confirmed to increase corneal layer moisture content of the skin and demonstrate superior moisturizing effects. In addition, the moisturizer of the present invention was confirmed to demonstrate effects that were superior to glycerin, which has conventionally been widely used as a moisturizer.

TABLE 1

Results of Rate of Change in Corneal Layer Moisture Content (%)

| | Day 3 | Day 5 |
|---|---|---|
| Example 1 | 156.6 | 147.2 |
| Comparative Example 1 | 118.7 | 120.7 |
| Comparative Example 2 | 114.7 | 121.9 |

[Solubility Evaluation]

Appearance and solubility were evaluated for N,N-dimethyl-2-(methylamino)acetoamide, N,N-dimethyl-2-(methylamino) acetoamide hydrochloride and sarcosine. The results are shown in Table 2. Furthermore, dissolution was evaluated based on appearance after preparing a solution at room temperature. The solubilities shown in the table indicate the concentration at which dissolution was confirmed, and those results shown with a ">" symbol in the table indicate the concentration at which the substance was confirmed to dissolve, and actual solubility is greater than or equal to this concentration.

TABLE 2

Appearance and Solubility

| Compound | Appearance (Room Temperature) | Solubility (%) | |
|---|---|---|---|
| | | Ethanol | Water |
| N,N-dimethyl-2-(methylamino)acetoamide | Liquid | >58 | >55 |
| N,N-dimethyl-2-(methylamino)acetoamide hydrochloride | White crystal | >14.1 | >77 |
| Sarcosine | White crystal | 0.10 | 71.5 |

The acetoamide compounds as claimed in the present invention were confirmed to be liquids, demonstrate high penetrability into the corneal layer, and can be expected to sustain moisturizing effects. Moreover, since both the acetoamide compound and hydrochloride thereof as claimed in the present invention demonstrate good solubility in water as well as ethanol, they can be easily formulated into a preparation and can be expected to demonstrate satisfactory low-temperature stability and usability.

On the other hand, although sarcosine demonstrates high solubility in water, it is poorly soluble in ethanol, and in the case of being incorporated in large amounts in compositions for external application to skin containing low amounts of water, was determined to have the risk of resulting in precipitation of crystals and having poor low-temperature stability.

[Anti-Wrinkle Evaluation]

A solution incorporating a wrinkle preventer/improver (Example 2) was applied to one of either the left or right eye having crow's feet while a liquid not incorporating a wrinkle preventer/improver (Comparative Example 3) was applied to the other eye of 26 healthy subjects having crow's feet ranging in age from 30 to 60 years old (mean age: 46 years). The compositions were applied three days a day for one month, and the forms of the crow's feet before and after application were using a Primos (GMF, Germany), which is a device for making measurements by projecting a lattice-shaped stratification pattern and observing from different angles. Areas containing wrinkles were extracted from the resulting three-dimensional images and a comparison was made of changes before and after application. The areas containing wrinkles were also extracted followed by calculation of wrinkle surface area ratio for comparison purposes.

Example 2

Containing Drug

| | |
|---|---|
| N,N-dimethyl-2-(methylamino)acetoamide hydrochloride | 1.0 wt % |
| Cosmetic alcohol | 5.0 |
| Dipropylene glycol | 2.0 |
| Dynamite glycerin | 1.0 |
| Phenoxyethanol | 0.5 |
| Polyoxyethylene-polyoxypropylene decyl tetradecyl ether | 0.1 |
| Citric acid | 0.04 |
| Sodium citrate | 0.1 |
| Trisodium edetate | 0.01 |
| Purified water | Remainder |

Comparative Example 3

Not Containing Drug

| | |
|---|---|
| Cosmetic alcohol | 5.0 |
| Dipropylene glycol | 2.0 |
| Dynamite glycerin | 1.0 |
| Phenoxyethanol | 0.5 |
| Polyoxyethylene-polyoxypropylene decyl tetradecyl ether | 0.1 |
| Citric acid | 0.04 |
| Sodium citrate | 0.1 |
| Trisodium edetate | 0.01 |
| Purified water | Remainder |

The results of three-dimensional analyses of crow's feet replicas and the mean values in the rate of change (%) of the surface area occupied by the crow's feet per square centimeter as determined by calculation are shown in FIG. 1. As can be understood from the drawing, although an increase in wrinkle surface area was not suppressed following application of Comparative Example 3, wrinkle surface area conversely decreased following application of Example 2.

Figure 2:
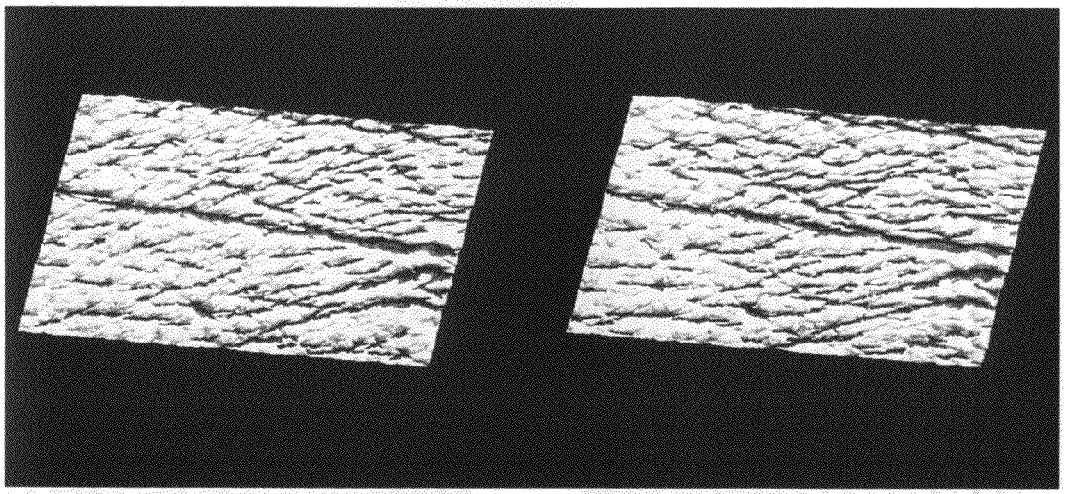
FIG. 2 shows three-dimensional analytical images as obtained with a Primos along with the results of calculating wrinkle surface area ratio as an example of remarkable wrinkle improving effects. Dark areas of the images indicate wrinkles.
Figure 2:
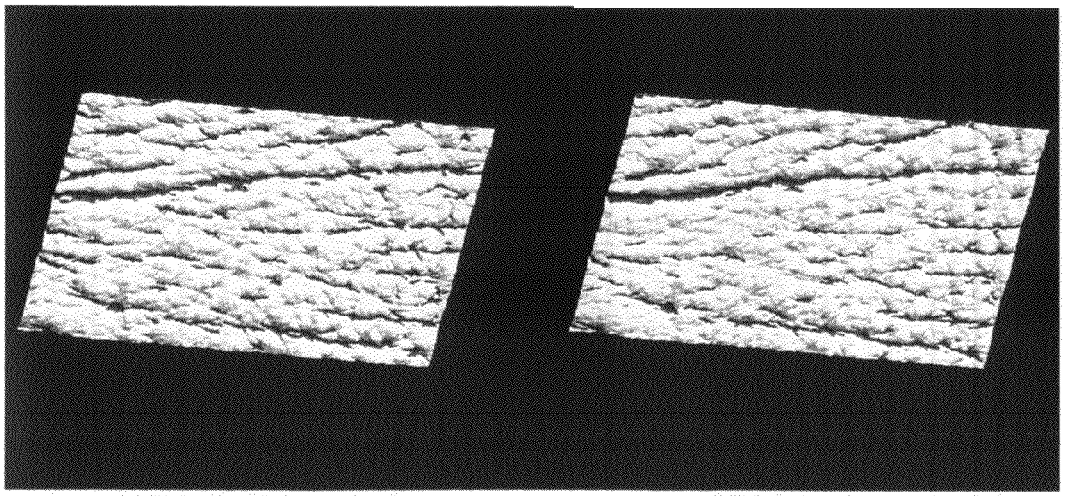

In addition, a remarkable example of wrinkle improving effects is shown in FIG. 2. In this manner, the composition for external application to skin incorporating an acetoamide compound as claimed in the present invention was confirmed to have superior wrinkle preventive and/or improving effects.

The following indicates compositions for external application to skin of the present invention as well as compositions for external application to skin as examples of moisturizers of the present invention. Furthermore, all of the compositions for external application to skin demonstrated superior moisturizing effects and wrinkle preventive and/or improving effects.

Formulation Example 1

| Cream | Wt % |
|---|---|
| Stearic acid | 5.0 |
| Stearyl alcohol | 4.0 |
| Isopropyl myristate | 18.0 |
| Glycerin monostearic acid ester | 3.0 |
| Propylene glycol | 10.0 |
| N,N-dimethyl-2-(methylamino)acetoamide hydrochloride | 3.0 |
| Potassium hydroxide | 0.2 |
| Sodium bisulfite | 0.01 |
| Preservative | As suitable |
| Fragrance | As suitable |
| Ion exchange water | Remainder |

Preparation Method: Propylene glycol and potassium hydroxide are added to ion exchange water and dissolved followed by heating and maintaining at 70° C. (aqueous phase). The other components are mixed and dissolved by heating followed by maintaining at 70° C. (oily phase). The oily phase is gradually added to the aqueous phase and once the entire amount has been added, the mixture is briefly maintained at that temperature to allow a reaction to occur. Subsequently, the mixture is uniformly emulsified with a homomixer and then cooled to 30° C. while stirring well.

Formulation Example 2

| Cream | Wt % |
|---|---|
| Stearic acid | 6.0 |
| Sorbitan (mono)stearate | 2.0 |
| Polyoxyethylene (20) sorbitan | 1.5 |
| Polyoxyethylene (20) sorbitan (mono)stearate Propylene glycol | 10.0 |
| N,N-dimethyl-2-(methylamino)acetoamide citrate | 7.0 |
| Glycerin trioctanoate | 10.0 |
| Squalene | 5.0 |
| Sodium bisulfite | 0.01 |
| Ethyl para-hydroxybenzoate | 0.3 |
| Fragrance | As suitable |
| Ion exchange water | Remainder |

Preparation Method: Propylene glycol is added to ion exchange water and dissolved followed by heating and maintaining at 70° C. (aqueous phase). The other components are mixed and dissolved by heating followed by maintaining at 70° C. (oily phase). The oily phase is added to the aqueous phase followed by carrying out preliminary emulsification, and after uniformly emulsifying with a homomixer, the mixture is cooled to 30° C. while stirring well.

Formulation Example 3

| Cream | Wt % |
| --- | --- |
| Stearyl alcohol | 7.0 |
| Stearic acid | 2.0 |
| Hydrogenated lanolin | 2.0 |
| Squalane | 5.0 |
| 2-octyldodecyl alcohol | 6.0 |
| Polyoxyethylene (25) cetyl alcohol ether | 3.0 |
| Glycerin monostearic acid ester | 2.0 |
| Propylene glycol | 5.0 |
| N,N-dimethyl-2-(methylamino)acetoamide | 0.001 |
| Fragrance | As suitable |
| Sodium bisulfite | 0.03 |
| Ethyl para-hydroxybenzoate | 0.3 |
| Ion exchange water | Remainder |

Preparation Method: Propylene glycol is added to ion exchange water and dissolved followed by heating and maintaining at 70° C. (aqueous phase). The other components are mixed and dissolved by heating followed by maintaining at 70° C. (oily phase). The oily phase is added to the aqueous phase followed by carrying out preliminary emulsification, and after uniformly emulsifying with a homomixer, the mixture is cooled to 30° C. while stirring well.

Formulation Example 4

| Milky Emulsion | Wt % |
| --- | --- |
| Stearic acid | 2.5 |
| Cetyl alcohol | 1.5 |
| Vaseline | 5.0 |
| Liquid paraffin | 10.0 |
| Polyoxyethylene (10) monooleic acid ester | 2.0 |
| Polyethylene glycol 1500 | 3.0 |
| Triethanolamine | 1.0 |
| N,N-dimethyl-2-(methylamino)acetoamide sulfate | 10.0 |
| Sodium bisulfite | 0.01 |
| Ethyl para-hydroxybenzoate | 0.3 |
| Carboxyvinyl polymer | 0.05 |
| Fragrance | As suitable |
| Ion exchange water | Remainder |

Preparation Method: Carboxyvinyl polymer is dissolved in a small amount of ion exchange water (A phase). Polyethylene glycol 1500 and triethanolamine are added to the remaining ion exchange water and dissolved by heating followed by maintaining at 70° C. (aqueous phase). The other components are mixed and dissolved by heating followed by maintaining at 70° C. (oily phase). The oily phase is added to the aqueous phase followed by carrying out preliminary emulsification, the A phase is added and after uniformly emulsifying with a homomixer, the mixture is cooled to 30° C. while stirring well following emulsification.

Formulation Example 5

| Milky Emulsion | Wt % |
| --- | --- |
| (Oily Phase) | |
| Stearyl alcohol | 1.5 |
| Squalene | 2.0 |
| Vaseline | 2.5 |
| Deodorized liquid lanolin | 1.5 |
| Evening primrose oil | 2.0 |
| Isopropyl myristate | 5.0 |
| Glycerin monooleate | 2.0 |
| Polyoxyethylene (60) hydrogenated castor oil | 2.0 |
| Tocopheryl acetate | 0.05 |
| Ethyl para-hydroxybenzoate | 0.2 |
| Butyl para-hydroxybenzoate | 0.1 |
| N,N-dimethyl-2-(methylamino)acetoamide phosphate | 1.0 |
| Fragrance | As suitable |
| (Aqueous Phase) | |
| Sodium bisulfite | 0.01 |
| Glycerin | 5.0 |
| Sodium hyaluronate | 0.01 |
| Carboxyvinyl polymer | 0.2 |
| Potassium hydroxide | 0.2 |
| Purified water | Remainder |

Preparation Method: Oily phase components are dissolved at 70° C. Aqueous phase components are dissolved at 70° C., the oily phase components are mixed into the aqueous phase components and after emulsifying with an emulsifier, the mixture is cooled to 30° C. with a heat exchanger.

Formulation Example 6

| Jelly | Wt % |
| --- | --- |
| 95% ethyl alcohol | 10.0 |
| Dipropylene glycol | 15.0 |
| Polyoxyethylene (50) oleyl alcohol ether | 2.0 |
| Carboxyvinyl polymer | 1.0 |
| Sodium hydroxide | 0.15 |
| L-arginine | 0.1 |
| N,N-dimethyl-2-(methylamino)acetoamide glutamate | 1.0 |
| Methyl para-hydroxybenzoate | 0.2 |
| Fragrance | As suitable |
| Ion exchange water | Remainder |

Preparation Method: Carboxyvinyl polymer is uniformly dissolved in ion exchange water, while polyoxyethylene (50) oleyl alcohol ether is dissolved in 95% ethanol and added to the aqueous phase. Next, after adding the other components, the mixture is neutralized and thickened with sodium hydroxide and L-arginine.

Formulation Example 7

| Essence | Wt % |
|---|---|
| (A Phase) | |
| Ethanol (95%) | 10.0 |
| Polyoxyethylene (20) octyldodecanol | 1.0 |
| Methyl para-hydroxybenzoate | 0.15 |
| Pantotenyl ethyl ether | 0.1 |
| N,N-dimethyl-2-(methylamino)acetoamide oxalate | 0.05 |
| (B Phase) | |
| Potassium hydroxide | 0.1 |
| (C Phase) | |
| Glycerin | 5.0 |
| Dipropylene glycol | 10.0 |
| Sodium bisulfite | 0.03 |
| Carboxyvinyl polymer | 0.2 |
| Purified water | Remainder |

Preparation Method: The A phase and C phase components are respectively uniformly dissolved followed by adding the A phase to the C phase and dissolving. Next, the B phase is added followed by filling.

Formulation Example 8

| Pack | Wt % |
|---|---|
| (A Phase) | |
| Dipropylene glycol | 5.0 |
| Polyoxyethylene (60) hydrogenated castor oil | 5.0 |
| (B Phase) | |
| N,N-dimethyl-2-(methylamino)acetoamide succinate | 1.0 |
| Olive oil | 5.0 |
| Tocopheryl acetate | 0.2 |
| Ethyl para-hydroxybenzoate | 0.2 |
| Fragrance | 0.2 |
| (C Phase) | |
| Sodium bisulfite | 0.03 |
| Polyvinyl alcohol (saponification: 90, polymerization: 2000) | 13.0 |
| Ethanol | 7.0 |
| Purified water | Remainder |

Preparation Method: The components of the A Phase, B Phase and C Phase are respectively uniformly dissolved followed by the addition of the B Phase to the A Phase and dissolving. Next, the C Phase is added thereto followed by filling.

Formulation Example 12

| Ointment | Wt % |
|---|---|
| Polyoxyethylene (30) cetyl ether | 2.0 |
| Glycerin monostearate | 12.0 |
| Liquid paraffin | 10.0 |
| Vaseline | 40.0 |
| Cetanol | 6.0 |
| Methyl para-hydroxybenzoate | 0.1 |
| Butyl para-hydroxybenzoate | 0.1 |
| N,N-dimethyl-2-(methylamino)acetoamide phenyl sulfate | 5.0 |
| Propylene glycol | 10.0 |
| Ion exchange water | Remainder |
| Fragrance | As suitable |

Preparation Method: Propylene glycol is added to ion exchange water and dissolved followed by heating and maintaining at 70° C. (aqueous phase). The other components are mixed and dissolved at 70° C. (oily phase). The oily phase is added to the aqueous phase and the mixture is uniformly emulsified with a homomixer followed by cooling and filling.

Formulation Example 10

| Cream | Wt % |
|---|---|
| Liquid paraffin | 8.0 |
| Vaseline | 3.0 |
| Dimethyl polysiloxane | 2.0 |
| Stearyl alcohol | 3.0 |
| Behenyl alcohol | 2.0 |
| Glycerin | 5.0 |
| Dipropylene glycol | 4.0 |
| Trehalose | 1.0 |
| Pentaerythrityl tetra-2-ethylhexanoate | 4.0 |
| Polyoxyethylene glyceryl monoisostearate | 2.0 |
| Polyoxyethylene glyceryl monostearate | 1.0 |
| Lipophilic glyceryl monostearate | 2.0 |
| Citric acid | 0.05 |
| Sodium citrate | 0.05 |
| Potassium hydroxide | 0.015 |
| Liposoluble licorice extract | 0.1 |
| Retinol palmitate (1 million units) | 0.25 |
| N,N-dimethyl-2-(methylamino)acetoamide hydrochloride | 1.0 |
| Tocopheryl acetate | 0.1 |
| Paraoxybenzoic acid ester | As suitable |
| Phenoxyethanol | As suitable |
| Dibutylhydroxytoluene | As suitable |
| Trisodium edetate | 0.05 |
| 4-t-butyl-4'-methoxydibenzoyl methane | 0.01 |
| 2-ethylhexyl para-methoxy cinnamate | 0.1 |
| β-carotene | 0.01 |
| Polyvinyl alcohol | 0.5 |
| Hydroxyethyl cellulose | 0.5 |
| Carboxyvinyl polymer | 0.05 |
| Purified water | Remainder |
| Fragrance | As suitable |

Formulation Example 11

| Cream | Wt % |
|---|---|
| Vaseline | 2.0 |
| Dimethyl polysiloxane | 2.0 |
| Ethanol | 5.0 |
| Behenyl alcohol | 0.5 |
| Batyl alcohol | 0.2 |
| Glycerin | 7.0 |
| 1,3-butylene glycol | 5.0 |
| Polyethylene glycol 20000 | 0.5 |
| Jojoba oil | 3.0 |
| Squalane | 2.0 |
| Phytosteryl hydroxystearate | 0.5 |
| Pentaerythrityl tetra-2-ethylhexanoate | 1.0 |
| Polyoxyethylene hydrogenated castor oil | 1.0 |
| Potassium hydroxide | 0.1 |
| Sodium pyrosulfite | 0.01 |
| Sodium hexametaphosphate | 0.05 |
| Stearyl glycyrrhetinate | 0.1 |
| Pantotenyl ethyl ether | 0.1 |
| Albutin | 7.0 |
| Tranexamic acid methyl amide hydrochloride | 11.0 |
| N,N-dimethyl-2-(methylamino)acetoamide fumarate | 1.0 |
| Tocopherol acetate | 0.1 |
| Sodium hyaluronate | 0.05 |
| Paraoxybenzoic acid ester | As suitable |
| Trisodium edetate | 0.05 |
| 4-t-butyl-4'-methoxydibenzoyl methane | 0.1 |
| Glyceryl diparamethoxy cinnamate mono-2-ethyl hexanoate | 0.1 |
| Yellow iron oxide | As suitable |
| Xanthan gum | 0.1 |
| Carboxyvinyl polymer | 0.2 |
| Purified water | Remainder |

Formulation Example 12

| Lotion | Wt % |
|---|---|
| 1,3-butylene glycol | 6.0 |
| Glycerin | 4.0 |
| Oleyl alcohol | 0.1 |
| POE(20) sorbitan monolauric acid ester | 0.5 |
| POE(15) lauryl alcohol ester | 0.5 |
| Ethanol | 10.0 |
| N,N-dimethyl-2-(methylamino)acetoamide | 0.3 |
| Purified water | Remainder |

Formulation Example 13

| Lotion | Wt % |
|---|---|
| (Alcohol Phase) | |
| Ethanol | 10.0 |
| Oleyl alcohol | 0.1 |
| POE(20) sorbitan monolauric acid ester | 0.5 |
| POE(15) lauryl ether | 0.5 |
| Preservative | As suitable |
| Fragrance | As suitable |
| (Aqueous Phase) | |
| N,N-dimethyl-2-(methylamino)acetoamide hydrochloride | 20.0 |
| 1,3-butylene glycol | 6.0 |
| Glycerin | 4.0 |
| Ion exchange water | Remainder |

Formulation Example 14

| Solid Powdery Foundation | Wt % |
|---|---|
| Talc | 15.0 |
| Sericite | 10.0 |
| Spherical nylon powder | 10.0 |
| Porous silicic anhydride powder | 15.0 |
| Boron nitride | 5.0 |
| Titanium dioxide | 5.0 |
| Iron oxide | 3.0 |
| Zinc stearate | 5.0 |
| N,N-dimethyl-2-(methylamino)acetoamide glutamate | 1.0 |
| Liquid paraffin | Remainder |
| Glycerin triisooctanoate | 15.0 |
| Sorbitan sesquioleate | 1.5 |
| Preservative | As suitable |
| Fragrance | As suitable |

Formulation Example 15

| Water-in-oil Emulsified Foundation | Wt % |
|---|---|
| Spherical nylon | 10.0 |
| Porous silicic anhydride powder | 8.0 |
| Titanated mica | 2.0 |
| Silicone-treated sericite | 2.0 |
| Silicone-treated mica | 12.0 |
| Silicone-treated titanium dioxide | 5.0 |
| Silicone-treated iron oxide | 2.0 |
| Ion exchange water | Remainder |
| N,N-dimethyl-2-(methylamino)acetoamide aspartate | 1.0 |
| Decamethyl cyclopentane siloxane | 18.0 |
| Dimethyl polysiloxane | 5.0 |
| Squalane | 1.0 |
| POE-modified dimethyl polysiloxane | 2.0 |
| Preservative | As suitable |
| Fragrance | As suitable |

All of the compositions for external application to skin obtained in Formulation Examples 1 to 14 demonstrated satisfactory moisturizing effects in the same manner as determined in Example 1, had superior wrinkle preventive and/or improving effects in the same manner as determined in Example 2, and demonstrated superior stability and usability.

The invention claimed is:

1. A composition for external application to skin containing one type or two or more types of compounds selected from the group consisting of aminoacetoamide compounds represented by the following general formula (1) and salts thereof.

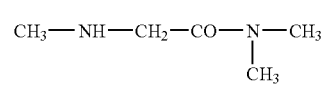

(1)

2. A moisturizer comprising one type or two or more types of compounds selected from the group consisting of the aminoacetoamide compounds and salts thereof.

3. A wrinkle preventer/improver comprising one type or two or more types of compounds selected from the group consisting of the aminoacetoamide compounds and salts thereof.

* * * * *